United States Patent
Kainz

(10) Patent No.: US 6,227,033 B1
(45) Date of Patent: May 8, 2001

(54) AUTO-CALIBRATION METHOD FOR A WIDE RANGE EXHAUST GAS OXYGEN SENSOR

(75) Inventor: Jeff Leon Kainz, Sterling Heights, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/268,199

(22) Filed: Mar. 11, 1999

(51) Int. Cl.$^7$ .......................... F02D 41/14; G01N 27/46; F01N 9/00; F01N 3/10
(52) U.S. Cl. ......................... 73/23.32; 73/1.06; 324/615; 123/674; 123/703
(58) Field of Search ................. 73/23.32, 1.06, 73/117.2, 31.02; 324/615; 123/682, 703, 674

(56) References Cited

U.S. PATENT DOCUMENTS

| | | | |
|---|---|---|---|
| 4,418,566 | * 12/1983 | Beck et al. ............................... | 73/23 |
| 5,265,458 | * 11/1993 | Usami et al. ......................... | 73/23.32 |
| 5,313,820 | *  5/1994 | Aylsworth .............................. | 73/24.01 |
| 5,323,635 | *  6/1994 | Ueno et al. ........................... | 73/23.32 |
| 5,347,474 | *  9/1994 | Wong ................................ | 364/571.02 |
| 5,524,472 | *  6/1996 | Hötzel ...................................... | 73/1 G |
| 5,535,135 | *  7/1996 | Bush et al. ............................ | 364/496 |
| 5,642,722 | *  7/1997 | Schumacher et al. ................ | 123/673 |
| 5,771,687 | *  6/1998 | Staufenberg et al. ................ | 60/274 |
| 5,877,413 | *  3/1999 | Hamburg et al. .................... | 73/118.1 |
| 5,901,691 | *  5/1999 | Katoh ................................... | 123/688 |
| 5,952,555 | *  9/1999 | Möbius ............................... | 73/23.32 |
| 5,970,967 | * 10/1999 | Uchikawa ............................ | 123/688 |

\* cited by examiner

Primary Examiner—Hezron Williams
Assistant Examiner—David J. Wiggins
(74) Attorney, Agent, or Firm—Vincent A. Cichosz

(57) ABSTRACT

An improved fuel control in which the transfer function of a wide-range exhaust gas oxygen sensor is automatically and periodically learned or re-learned in the course of vehicle operation. The oxygen sensor is calibrated at two different operating conditions: at a stoichiometric air/fuel ratio, and at a fuel cut-off or free-air ratio. The first operating condition occurs during steady state operation when a switching sensor disposed in the exhaust gas stream downstream of the catalytic converter indicates that the engine is being fueled at the stoichiometric air/fuel ratio. The second operating condition occurs when engine fuel is shut off, either during vehicle deceleration, or when the engine is turned off. Once both calibration points have been determined, the transfer function of the wide range sensor is adjusted to match the stored voltages, and engine fueling is thereafter based on the adjusted transfer function.

10 Claims, 3 Drawing Sheets

AUTO-CALIBRATION METHOD FOR A WIDE RANGE EXHAUST GAS OXYGEN SENSOR

TECHNICAL FIELD

This invention relates to an automotive engine fuel control including a wide range oxygen sensor in the exhaust gas stream, and more particularly a control method for using an auxiliary switching oxygen sensor to automatically calibrate the wide range oxygen sensor.

BACKGROUND OF THE INVENTION

Effective emission control of internal combustion engine exhaust gases with a catalytic converter requires precise control of the air/fuel ratio supplied to the engine cylinders. For this purpose, it is customary to install an oxygen sensor in the engine exhaust pipe, and to use the sensor output as a feedback signal for closed-loop fuel control.

In general, two different types of oxygen sensors are available for usage in automotive fuel control. The most common and least expensive sensor, referred to as a switching sensor, has a bi-stable output voltage that switches or toggles between first and second states corresponding to lean and rich conditions of the sensed exhaust gas, relative to a stoichiometric air/fuel ratio of approximately 14.7:1 for pump gasoline. The other type of oxygen sensor, referred to as a universal exhaust gas oxygen sensor, or wide-range oxygen sensor, has an analog output that varies in amplitude in relation to the deviation of the sensed exhaust gas from the stoichiometric air/fuel ratio. Of the two sensor types, the switching sensor is less expensive but provides limited information, whereas the wide-range sensor enables improved fuel control performance.

A portion of cost of the wide-range sensor is related to calibration; typically, the calibration is performed off-line by the sensor manufacturer, and active or passive elements in the sensor wiring harness are selected or programmed to provide a standard output voltage vs. air/fuel ratio transfer function. A related disadvantage of the wide-range sensor is that the sensor characteristics may tend to drift with age and/or other factors, leading to fuel control errors since the one-time calibration cannot account for the drift.

SUMMARY OF THE INVENTION

The present invention is directed to an improved fuel control in which the transfer function of a wide-range exhaust gas oxygen sensor is automatically and periodically learned or calibrated in the course of vehicle operation. The auto-calibration method reduces the sensor cost to enable high performance fuel control at a lower cost, and periodically updates the calibration so that the improved performance can be achieved in spite of sensor drift due to age or other factors.

According to the invention, the engine fuel control is based on the output of a wide range oxygen sensor, which is automatically and periodically calibrated at two different operating conditions. The first operating condition occurs during steady state operation when a switching sensor disposed in the exhaust gas stream downstream of the catalytic converter indicates that the engine is being fueled at the stoichiometric air/fuel ratio. The second operating condition occurs either during vehicle deceleration when engine fueling is cut off or when the engine is turned off. The wide range sensor voltage developed under the first operating condition is stored as a stoichiometry calibration, and the wide range sensor voltage developed under the second operating condition is stored as a "free air" calibration. Once both calibration points have been determined, the transfer function of the wide range sensor is adjusted to match the stored voltages, and engine fueling is thereafter based on the adjusted transfer function. In a first embodiment, a characteristic transfer function stored in the controller in the form of a mathematical model or look-up table is shifted so as to intersect, as nearly as possible, the two determined calibration points. In a second embodiment, the controller effectively re-constructs the transfer function by incrementally adjusting the engine fueling with respect to the determined calibration points, and recording the corresponding sensor output voltages.

BRIEF DESCRIPTION OF THE DRAWINGS

FIG. 4A illustrates a transfer function error prior to auto-calibration, FIG. 4B illustrates an auto-calibration according to the first embodiment of this invention, and FIG. 4C illustrates an auto-calibration according to the second embodiment of this invention.

DESCRIPTION OF THE PREFERRED EMBODIMENT

Figure 1:
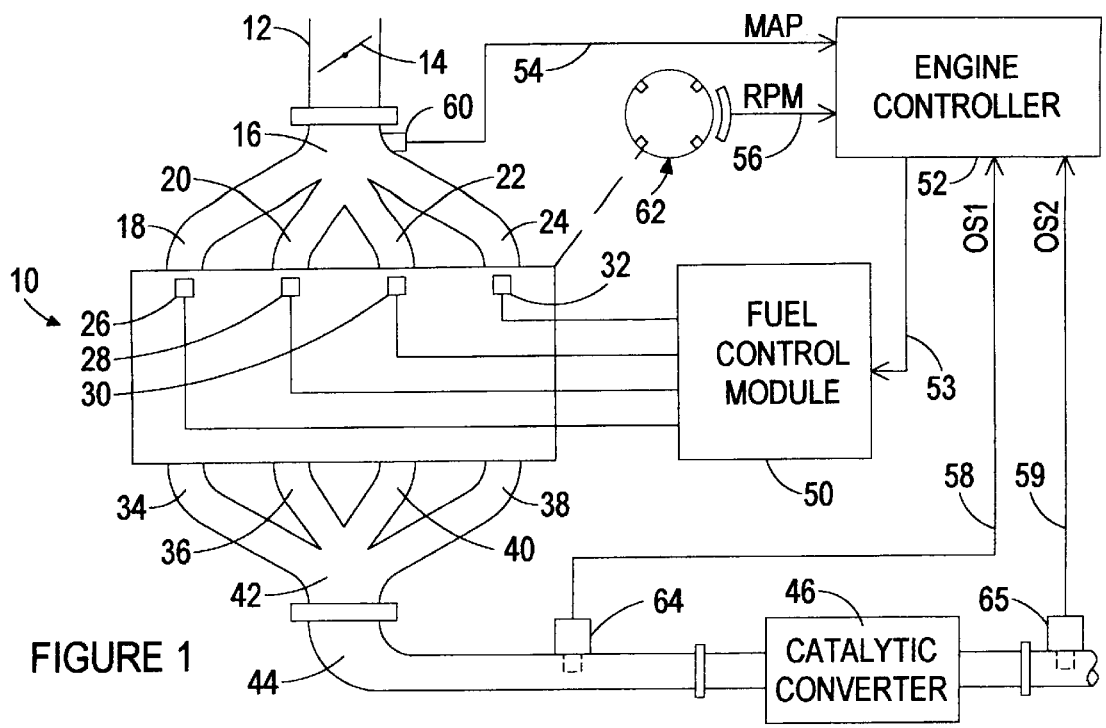
FIG. 1 is a schematic diagram of an internal combustion engine and exhaust system according to this invention, including an electronic engine controller, a wide-range oxygen sensor and a switching oxygen sensor.

Referring to the drawings, and particularly to FIG. 1, the reference numeral 10 generally designates an automotive four-cylinder internal combustion engine. Engine 10 receives intake air through an intake passage 12 that is variably restricted by a moveable throttle valve 14. Downstream of throttle valve 14, the intake air enters an intake manifold 16 for distribution to the individual engine cylinders (not shown) via a plurality of intake runners 18–24. The fuel injectors 26–32 are positioned to deliver a predetermined determined quantity of fuel to each intake runner 18–24 for combination with the intake air and admission to respective engine cylinders for combustion therein. The combustion products from each cylinder are exhausted into respective exhaust runners 34–40 of an exhaust manifold 42, and combined in an exhaust pipe 44, which in turn, is coupled to a catalytic converter 46 for emission control purposes.

The fuel injectors 26–32 are electrically activated by a fuel control module 50 under the control of a microprocessor based engine controller 52. Specifically, the controller 52 develops a fuel command pulse width, or injector on-time, for each of the engine cylinders, and provides the pulse width commands to fuel control module 50 via line 53, and the fuel control module activates the injectors 26–32 accordingly. The fuel pulse widths are determined in response to a number of inputs, including a manifold absolute pressure (MAP) signal on line 54, an engine speed (RPM) signal on line 56, and an oxygen sensor signal OS1 on line 58. The MAP signal is obtained with a conventional manifold absolute pressure sensor 60 responsive the pressure of the intake air in intake manifold 16, the RPM signal may be obtained from a conventional crankshaft or camshaft sensor, generally designated by the reference numeral 62, and the oxygen signal OS1 is obtained from a conventional universal exhaust gas or wide-range oxygen sensor 64 responsive to the exhaust gasses upstream of the catalytic converter 46 in exhaust pipe 44. A second oxygen sensor 65 of the type having an output that switches or toggles between first and second states corresponding to lean and rich conditions of the sensed exhaust gas relative to a stoichiometric air/fuel ratio is disposed in the exhaust gasses downstream of the catalytic converter 46, and is used for calibration of the wide-range sensor 64 as described below. The oxygen sensor 65 provides an output signal OS2 to controller 52 on line 59.

Figure 4A:
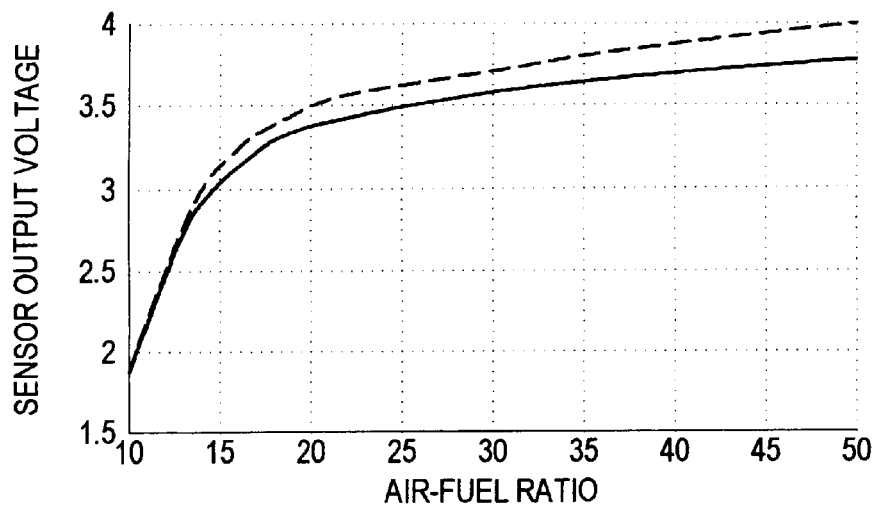
FIGS. 4A, 4B and 4C graphically depict the wide range sensor output voltage as a function of air/fuel ratio.

In general, the engine controller 52 determines a base fuel pulse width as a function of the RPM and MAP signals, and other inputs such as temperature and barometric pressure. Alternatively, the base fuel pulse width may be determined based on a measure of mass air flow in the intake passage 12, using a mass air flow meter up-stream of throttle plate 14. The controller 52 then adjusts the base fuel pulse width using previously learned closed-loop corrections, which are typically stored in a electrically-erasable non-volatile look-up table of controller 52 as a function of RPM and MAP. In a global type of fuel control, the adjusted base fuel pulse width is then supplied to the fuel control module 50, which activates each of the injectors 26–32 (either sequentially or concurrently) for an on-time corresponding to the adjusted base fuel pulse width. In an individual cylinder fuel control, samples of the output voltage of oxygen sensor 64 are associated with individual engine cylinders, and used to individually adjust the fueling for each engine cylinder. In either case, the wide range oxygen sensor 64 enables very accurate control of the fueling, when properly calibrated, since it indicates both the direction and magnitude of air/fuel ratio error. However, if the calibration is in error, there will be corresponding fueling errors, and the emission control may be degraded. An example of a calibration error is graphically depicted in FIG. 4A, where the true transfer function of wide-range oxygen sensor 64 is given by the solid trace, and the factory calibration is given by the broken trace. In the illustration, a sensor output of OS1=3.5V is interpreted as an air/fuel ratio of 20, as opposed to the actual ratio of 25.

According to this invention, the wide-range oxygen sensor is automatically and periodically calibrated, both at stoichiometric fueling during steady state operation, and at fuel cutoff during vehicle deceleration. Once both calibration points have been determined, the transfer function of the wide range sensor is adjusted to match the stored points, and engine fueling is thereafter based on the adjusted transfer function. In a first embodiment, a characteristic transfer function stored in the controller in the form of a mathematical model or look-up table is adjusted so as to intersect, as nearly as possible, the two determined calibration points. In a second embodiment, the controller incrementally adjusts the engine fueling with respect to the determined calibration points, and records the corresponding sensor output voltages, effectively re-constructing the transfer function.

Figure 2:
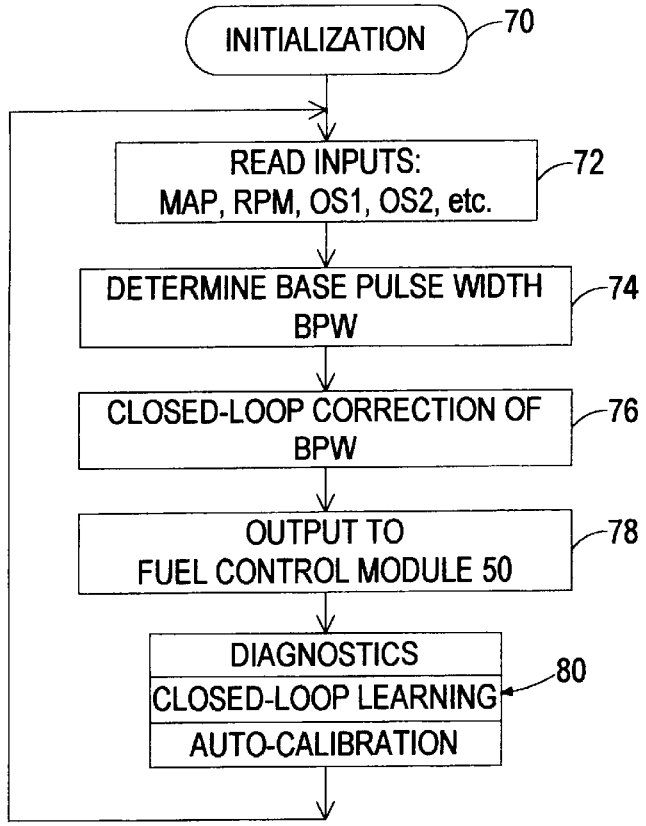
FIGS. 2 and 3 are flow diagrams representative of computer program instructions executed by the engine controller of FIG. 1 in carrying out fuel control and the automatic sensor calibration method of this invention.
Figure 3:
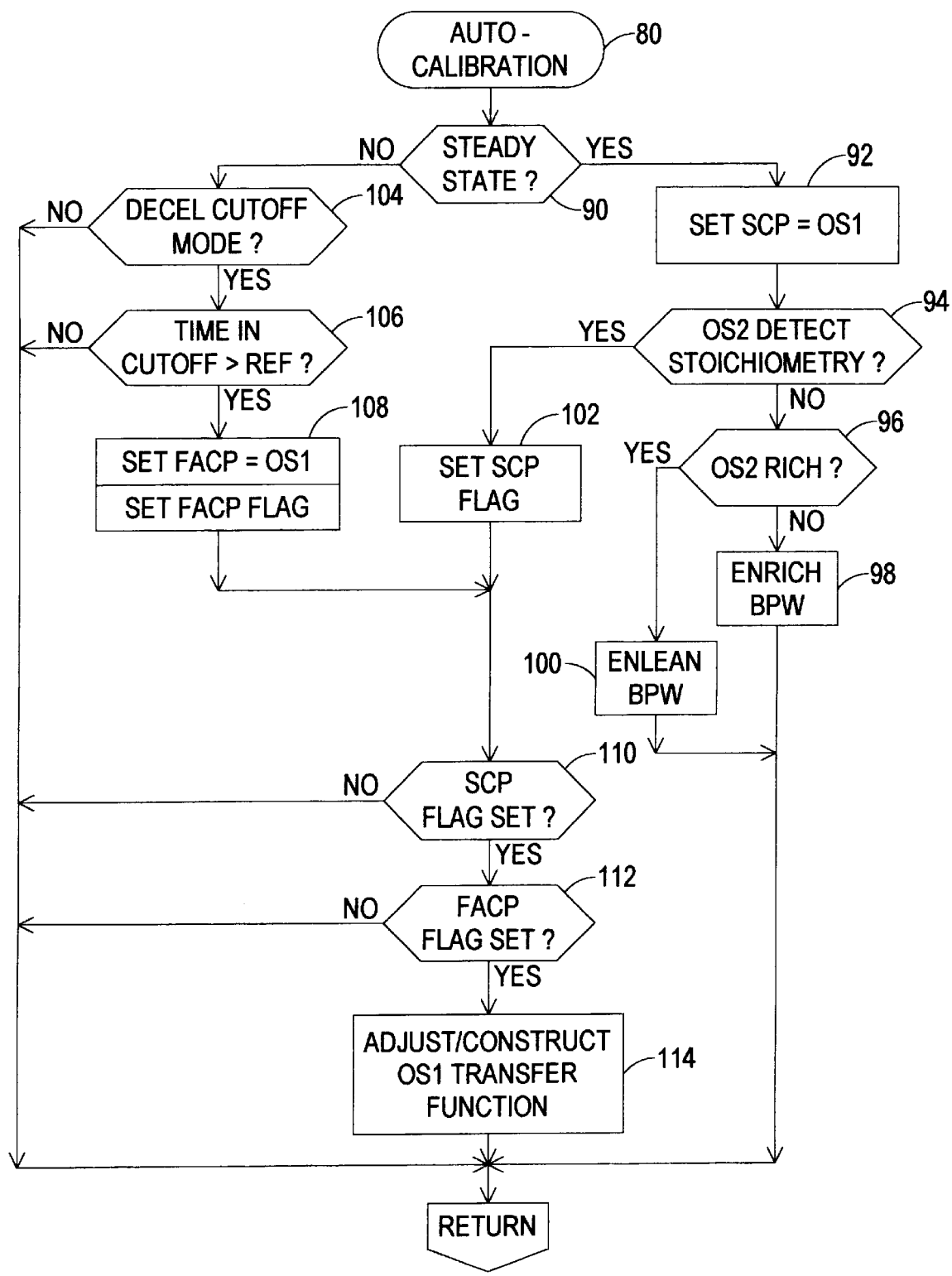

FIGS. 2–3 are flow diagrams representative of computer program instructions executed by the controller 52 in carrying out the automatic sensor calibration of this invention. FIG. 2 is a simplified main or executive flow diagram, whereas FIG. 3 is a more detailed flow diagram concerning the automatic calibration method of this invention.

Referring to FIG. 2, the block 70 designates a series of initialization instructions for initializing the operation of the controller 52 at the beginning of each period of vehicle operation. This may include, for example, resetting various flags and registers to predetermined states, as will be well known to those skilled in the art of engine control. Following initialization, the blocks 72–80 are repeatedly executed in sequence as shown. At block 72, the controller 52 reads various input signals, including the MAP and RPM signals, and the outputs OS1 and OS2 of oxygen sensors 64 and 65. Other input signals, such as barometric pressure and manifold inlet temperature are also typically obtained at this point. Based on the various inputs, the controller 52 then determines a base fuel pulse width (BPW) as indicated at block 74. Typically, the base pulse width is stored in a non-volatile look-up table as a function of MAP and RPM as mentioned above, and other parameters such as barometric pressure are used to modify the determined BPW value. As noted at block 76, a closed-loop correction is then applied to the BPW value in order to adaptively adjust the engine air/fuel ratio, based on the information contained in the OS1 oxygen sensor input. Typically, the closed-loop pulse width corrections are also stored as a function of MAP and RPM in a non-volatile look-up table, generally referred to as block learning memory, or BLM. At block 78, the controller 52 outputs the corrected fuel pulse width to the fuel control module 50, which in turn, correspondingly activates the fuel injectors 26–32, either concurrently, or in sequence. At block 80, the controller 52 executes one or more background functions, which may include diagnostics, closed-loop air/fuel ratio learning, and the auto-calibration function of this invention. Alternatively, the background functions may be executed in response to periodically generated interrupt requests, as is well known.

The flow diagram of FIG. 3 details the auto-calibration function referenced in block 80 of FIG. 2. As indicated above, this involves determining two calibration points: one at stoichiometry, and one at fuel cutoff. The calibration point at stoichiometry is referred to herein as the Stoichiometric Calibration Point, or SCP, whereas the calibration point at fuel cutoff is referred to herein as the Free Air Calibration Point, or FACP.

With respect to the determination of the SCP, block 90 is first executed to determine if the engine 10 is in a steady state operating condition; this may be determined, for example, by detecting a condition of steady throttle and speed, and an engine temperature within specified limits. If the engine 10 is operating in steady state, the blocks 92 and 94 are executed to set the SCP to the OS1 reading of wide-range oxygen sensor 64, and to determine if the OS2 reading of the switching oxygen sensor 65 confirms the presence of a stoichiometric air/fuel ratio. If the OS2 reading is not indicative of stoichiometry, the blocks 96–100 incrementally adjust the base pulse width BPW in a direction to drive the air/fuel ratio toward the stoichiometric switching point of oxygen sensor 65. Thus, if block 96 determines that the air/fuel ratio is lean relative to the stoichiometric ratio, the block 98 incrementally increases BPW to enrich the air/fuel ratio; conversely, if block 96 determines that the air/fuel ratio is rich relative to the stoichiometric ratio, the block 100 incrementally decreases BPW to en-lean the air/fuel ratio. In the next execution of the main flow diagram of FIG. 2, the air/fuel ratio will change accordingly, and if engine 10 is still operating in steady state (as determined at block 90), blocks 92–94 are re-executed to revise the SCP based on the OS1 reading and to determine if the incremental fuel adjustment of the previous loop caused the OS2 reading of oxygen sensor 65 to indicate stoichiometric operation. So long as steady-state engine operation is maintained, the BPW is repeatedly adjusted by blocks 98 or 100 until block 94 is answered in the affirmative. At such point, block 102 is executed to set the SCP Flag, indicating that the SCP has been determined.

With respect to determination of the FACP, the block 104 is first executed to determine if the engine 10 is in a condition of fuel cutoff, as may periodically occur during sustained high speed vehicle deceleration, depending on the design of the engine fuel control algorithms. If the engine 10 has been in a fuel cut-off condition for more than a reference time REF corresponding to the anticipated lag in response of the wide-range oxygen sensor 64, as determined at block 106, the block 108 is executed to set the FACP to the OS1 reading of sensor 64 and to set the FACP Flag, indicating that the FACP has been determined.

Figure 4B:
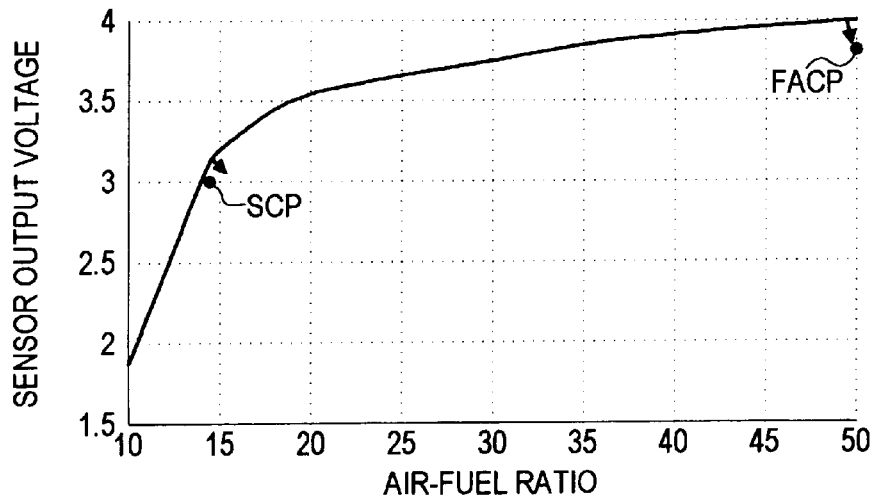
Figure 4C:
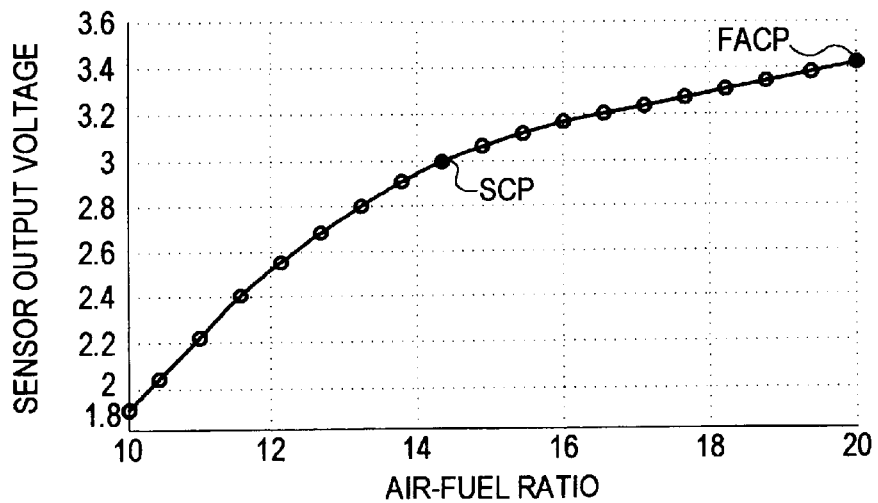

Once either of the SCP or FACP Flags have been set, the blocks 110 and 112 are executed to determine if both flags have been set. When both flags have been set, the controller 52 executes the block 114 to adjust/construct the transfer function of the wide range oxygen sensor 64. There are at least two ways this can be done. According to a first embodiment, graphically illustrated in FIG. 4B, the controller 52 adjusts a generic or characteristic transfer function (which may be described by mathematical model or stored values in a look-up table) so that it intersects the SCP and FACP. Another related technique is to use a least squares polynomial fit algorithm to develop the transfer function based on the determined SCP and FACP. The limitation of these approaches is that a characteristic shape of the transfer function is assumed. Ordinarily, this may be a reasonable assumption, and the adjusted transfer function will be close enough to provide the desired fueling accuracy. However, if the characteristic shape of the transfer function tends to change with age and/or other factors, a second embodiment of this invention, graphically illustrated in FIG. 4C, may be utilized to effectively construct the transfer function by incrementally adjusting the engine fueling with respect to the determined SCP and FACP, and recording the corresponding OS1 readings. For example, once the SCP is determined, the BPW may be increased by a predetermined or calculated amount to produce an air/fuel ratio of 14.0 instead of the stoichiometric ratio of 14.7, resulting in an OS1 reading of 2.9 instead of 3.0. Thus, the OS1 readings taken as the BPW is incrementally adjusted relative to the determined SCP and FACP reveal the true shape of the oxygen sensor transfer function. Since the calibration tends to be more critical at air/fuel ratios higher than stoichiometry (for so-called lean burn fuel control), a straight line approximation may be utilized between the SCP and FACP if desired in order to reduce the time required to construct the transfer function.

In summary, the present invention provides a method of automatically calibrating a wide range oxygen sensor by utilizing an auxiliary switching oxygen sensor and fuel cutoff deceleration control in order to realize improved fueling accuracy afforded by the sensor information. The cost of the sensor is reduced compared to prior factory calibration techniques, since the auxiliary switching sensor is inexpensive, and already present in many applications for diagnostic or other purposes. While this invention has been described in reference to the illustrated embodiment, it is expected that various modifications in addition to those suggested above will occur to those skilled in the art. In this regard, it will be understood that the scope of this invention is not limited to the illustrated embodiment, and that sensor calibration methods incorporating such modifications may fall within the scope of this invention, which is defined by the appended claims.

What is claimed is:

1. A method of automatically learning a transfer function of a wide range oxygen sensor disposed in exhaust gases of a vehicle engine to sense an air/fuel ratio of said engine, the method comprising the steps of:

detecting independently of said wide range oxygen sensor when the air/fuel ratio of said engine corresponds to a stoichiometric ratio;

establishing a first calibration point corresponding to an output voltage of said wide range oxygen sensor when the stoichiometric ratio is detected;

detecting a condition of fuel cutoff during operation of said engine;

establishing a second calibration point corresponding to an output voltage of said wide range oxygen sensor when the condition of fuel cutoff is detected; and determining the transfer function of said wide range oxygen sensor based on the established first and second calibration points.

2. The method set forth in claim 1, wherein the step of detecting when the air/fuel ratio of said engine corresponds to a stoichiometric ratio includes the steps of:

providing a switching oxygen sensor having an output signal that switches between first and second states relative to the stoichiometric ratio; disposing said switching oxygen sensor in the exhaust gasses of said engine; and detecting a stoichiometric air/fuel ratio based on the output signal of said switching oxygen sensor.

3. The method set forth in claim 1, including the steps of: detecting a deviation from the stoichiometric air/fuel ratio based on the output signal of said switching oxygen sensor, and in response to such detection:

incrementally adjusting a fuel amount supplied to said engine in a direction to drive the air/fuel ratio closer to the stoichiometric ratio; and repeating the steps of detecting when the air/fuel ratio of said engine corresponds to the stoichiometric ratio, and establishing the first calibration point when the stoichiometric ratio is detected.

4. The method set forth in claim 3, wherein the step of incrementally adjusting the fuel amount comprises incrementally increasing the fuel amount when the detected deviation corresponds to an air/fuel ratio greater than said stoichiometric ratio.

5. The method set forth in claim 3, wherein the step of incrementally adjusting the fuel amount comprises incrementally decreasing the fuel amount when the detected deviation corresponds to an air/fuel ratio less than said stoichiometric ratio.

6. The method set forth in claim 1, including the steps of: detecting whether the engine is in a steady state mode of operation; and allowing the establishment of said first calibration point only when said steady state mode of operation is detected.

7. The method set forth in claim 1, wherein said step of detecting a condition of fuel cutoff includes the steps of:

measuring a duration of said condition of fuel cutoff; and allowing the establishment of said second calibration point only when said measured duration exceeds a reference time corresponding to a response characteristic of said wide range oxygen sensor.

8. The method set forth in claim 1 wherein the step of determining the transfer function of said wide range oxygen sensor based on the established first and second calibration points includes the steps of:

storing a characteristic transfer function of said wide range oxygen sensor; and adjusting the stored transfer function in a manner to intersect the established first and second calibration points.

9. The method set forth in claim 1 wherein the step of determining the transfer function of said wide range oxygen sensor based on the established first and second calibration points includes the steps of:

incrementally adjusting a fuel amount supplied to the engine relative to at least one of the established first and second calibration points;

recording the output voltages of said wide range oxygen sensor corresponding to each adjustment of said fuel amount; and associating the recorded output voltages with air/fuel ratios corresponding to respective fuel amounts, thereby to determine said transfer function.

10. The method set forth in claim 1, wherein the steps of establishing the first and second calibration points and determining the transfer function of said wide range oxygen sensor are periodically repeated to re-learn said transfer function.

* * * * *